(12) United States Patent
Amano et al.

(10) Patent No.: US 7,373,929 B2
(45) Date of Patent: May 20, 2008

(54) FUEL NATURE MEASURING DEVICE OF INTERNAL COMBUSTION ENGINE AND INTERNAL COMBUSTION ENGINE HAVING THE SAME

(75) Inventors: Noriyasu Amano, Gamagori (JP);
Takanobu Kawano, Obu (JP);
Nobuhiko Koyama, Nagoya (JP)

(73) Assignees: Nippon Soken, Inc., Nishio (JP);
Denso Corporation, Kariya (JP)

( * ) Notice: Subject to any disclaimer, the term of this patent is extended or adjusted under 35 U.S.C. 154(b) by 0 days.

(21) Appl. No.: 11/889,241

(22) Filed: Aug. 10, 2007

(65) Prior Publication Data
US 2007/0289365 A1    Dec. 20, 2007

Related U.S. Application Data

(62) Division of application No. 11/194,657, filed on Aug. 2, 2005, now Pat. No. 7,272,485.

(30) Foreign Application Priority Data

Aug. 6, 2004    (JP)    .............................. 2004-230997

(51) Int. Cl.
*F02M 51/00*    (2006.01)
*F02M 33/02*    (2006.01)

(52) U.S. Cl. ........................ 123/491; 123/520; 701/103

(58) Field of Classification Search ................ 123/491, 123/494, 516–521; 701/101, 103, 104; 73/118.2
See application file for complete search history.

(56) References Cited

U.S. PATENT DOCUMENTS

| | | | |
|---|---|---|---|
| 5,140,965 A | | 8/1992 | Nogi et al. .................. 123/494 |
| 5,188,085 A | | 2/1993 | Habaguchi et al. ......... 123/520 |
| 5,295,472 A | * | 3/1994 | Otsuka et al. ............... 123/520 |
| 5,426,938 A | * | 6/1995 | Ogawa et al. ................. 60/285 |
| 5,483,935 A | * | 1/1996 | Ogawa et al. ......... 123/406.47 |

(Continued)

FOREIGN PATENT DOCUMENTS

JP    4-8956    1/1992

(Continued)

OTHER PUBLICATIONS

U.S. Appl. No. 11/889,242, filed Aug. 2007, Amano et al.

*Primary Examiner*—John T Kwon
(74) *Attorney, Agent, or Firm*—Nixon & Vanderhye P.C.

(57) ABSTRACT

A fuel nature measuring device for measuring the nature of fuel stored in a fuel tank includes a measurement passage, a gas flow generator, a pressure detector, an concentration operator, a temperature detector, and a volatility calculator. The measurement passage has an orifice. The gas flow generator generates gas flow in the measurement passage. The pressure detector detects a differential pressure between opposite ends of the orifice. The concentration operator determines a concentration of evaporated fuel in the fuel tank based on the differential pressure detected when the opposite ends of the measurement passage communicate with the fuel tank and the fuel flows in the measurement passage. The temperature detector determines a temperature of the fuel in the fuel tank. The volatility calculator calculates a volatility of the fuel in the fuel tank based on the concentration of the evaporated fuel and the temperature of the fuel in the tank.

4 Claims, 14 Drawing Sheets

U.S. PATENT DOCUMENTS

| | | |
|---|---|---|
| 5,542,394 A | 8/1996 | Tomisawa .................. 123/491 |
| 6,196,203 B1 | 3/2001 | Grieve et al. ............... 123/520 |
| 6,223,732 B1 * | 5/2001 | Isobe et al. ................. 123/520 |
| 6,314,944 B1 | 11/2001 | Majima ...................... 123/491 |
| 6,354,143 B1 * | 3/2002 | Isobe et al. ................. 73/49.7 |
| 6,363,919 B1 * | 4/2002 | Isobe et al. ................. 123/520 |
| 6,405,718 B1 * | 6/2002 | Yoshioka et al. .......... 123/520 |
| 6,817,232 B2 * | 11/2004 | Amano et al. ............. 73/118.1 |
| 7,272,485 B2 | 9/2007 | Amano et al. |
| 2005/0211228 A1 | 9/2005 | Amano et al. .............. 123/520 |
| 2006/0031000 A1 | 2/2006 | Amano et al. .............. 701/114 |
| 2006/0042605 A1 | 3/2006 | Amano et al. .............. 123/520 |

FOREIGN PATENT DOCUMENTS

JP        7-198710        8/1995

* cited by examiner

FUEL NATURE MEASURING DEVICE OF INTERNAL COMBUSTION ENGINE AND INTERNAL COMBUSTION ENGINE HAVING THE SAME

CROSS REFERENCE TO RELATED APPLICATIONS

This application is a divisional of application Ser. No. 11/194,657, filed on Aug. 2, 2005, now U.S. Pat. No. 7,272,485 which is based upon and claims the benefit of priority of Japanese Patent application Ser. No. 2004-230997, filed on Aug. 6, 2004, the contents of both applications are incorporated herein by reference.

FIELD OF THE INVENTION

The present invention relates to a fuel nature measuring device for an internal combustion engine and an internal combustion engine having the same.

BACKGROUND OF THE INVENTION

A gasoline engine in an automobile generally has a fuel injection valve provided at an intake pipe, and fuel injected from the fuel injection valve is supplied to an intake port. However, during cold starting with no sufficient warm-up, part of the fuel injected from the fuel injection valve tends to stick to the inner wall surface of the intake port or the surface of the intake valve and fails to enter the combustion chamber. This substantially reduces the injection amount. In order to secure an air-fuel ratio equivalent to that in a sufficiently warmed-up state, the injection amount is often corrected by adding fuel in such a case.

The amount of fuel thus sticking, for example, to the inner wall surface of the intake port, without contributing to combustion varies depending on the nature of the fuel, especially the level of its volatility. Fuel nature varies among the manufacturers, the seasons, and the distribution areas even if the fuel is of the same kind. Therefore, fuel nature must be measured highly precisely in order to accurately correct the injection amount.

A known technique for measuring fuel nature takes advantage of the characteristic that the dielectric constant of fuel changes depending on the fuel nature. According to this technique, a capacitor-type detector is provided and determines whether the fuel is light gasoline or heavy gasoline based on a capacitance of the detector corresponding to the dielectric constant of the fuel (see Japanese Utility Model Laid-Open Publication No. Hei 4-8956). According to this technique, an oscillation circuit that generates a signal at a frequency corresponding to capacitance is provided to obtain the capacitance. Another known technique takes advantage of the characteristic that the refractive index, boiling point, and molecular heat of a fuel changes depending on the fuel nature (see Japanese Patent Laid-Open Publication No. Hei 4-1438). According to the disclosure of Japanese Patent Laid-Open Publication No. Hei 4-1438, an optical fiber is immersed in the fuel, and the quantity of light passed through the optical fiber is analyzed to obtain the refractive index.

In order to obtain the volatility of fuel based on the dielectric constant and the refractive index, a relation between the dielectric constant and refractive index of the fuel and the volatility of the fuel must be previously known. However, the relationship varies among the manufacturers of the fuel, the seasons, and the distribution areas and it is not necessarily easy to acquire accurate information between them.

SUMMARY OF THE INVENTION

The embodiments of the present invention are directed to solve the above-described and other problems and provide a fuel nature measuring device for use in an internal combustion engine that can simply determine the volatility of fuel and an internal combustion engine having the same.

A fuel nature measuring device according to one aspect of the present invention measures the nature of fuel stored in a fuel tank. The measuring device includes a measurement passage having an orifice; a gas flow generating means for generating a gas flow in the measurement passage; differential pressure detecting means for detecting a differential pressure between both ends of the orifice; evaporated fuel concentration operating means for determining the concentration of evaporated fuel based on the differential pressure detected when the measurement passage communicates with the fuel tank at its both ends and gas in the fuel tank is the gas for measurement let to flow in the measurement passage; temperature detecting means for detecting a temperature of the fuel in the fuel tank; and volatility calculation means for calculating volatility of the fuel in the fuel tank as the fuel nature based on the concentration of the evaporated fuel detected by the evaporated fuel concentration operation means and the temperature detected by the temperature detecting means.

When the volatility of the fuel changes, the characteristic line of the saturated concentration of the evaporated fuel relative to the temperature changes. Based on the evaporated fuel concentration at the present temperature, the volatility of the fuel stored in the fuel tank can be specified.

According to another aspect of the present invention, the internal combustion engine includes a canister storing an absorbent that temporarily absorbs the evaporated fuel guided from the fuel tank through a conduit; a purge passage that guides gas in the canister including evaporated fuel desorbed from the absorbent into the intake pipe of the internal combustion engine and purges the evaporated fuel; and a purge control valve provided in the purge passage to adjust a purge flow rate.

The configuration also includes another evaporated fuel concentration operation means for operating a concentration of the evaporated fuel in gas for measurement based on the differential pressure detected when the measurement passage communicates with the canister at its both ends and gas in the canister is the gas for measurement let to flow in the measurement passage.

The main means for measuring the concentration of the evaporated fuel such as the measurement passage and the differential pressure detecting means can also be used for measuring the concentration of the evaporated fuel purged from the canister. In this way, the concentration of the evaporated fuel in the purge gas as well as the volatility of the fuel can be measured without having to provide a complicated configuration.

Another aspect of the present invention includes measurement passage switching means for switching between first and second concentration measurement states. In the first concentration measurement state, the measurement passage is opened to the atmosphere at its both ends and the gas passed through the measurement passage is the air. In the second concentration measurement state, the measurement passage communicates with the fuel tank at its both ends through a gas phase portion of the fuel tank and the gas let to flow in the fuel measurement passage is the gas in the fuel tank. The evaporated fuel concentration operating means serves as operation means for operating the concentration of the evaporated fuel based on the detected differential pressures in the first and second concentration measurement states.

In addition to the differential pressure detected when the gas in the fuel tank is distributed in the measurement passage, the differential pressure detected when the concentration of the evaporated fuel is known (zero) is available, so that correction can be carried out based on the differential pressure detected in the state. In this way, the fuel nature can be obtained more accurately.

Another aspect of the present invention includes valve means for blocking the gas flow at the orifice, and the differential pressure detecting means includes a pair of lead passages having the orifice and the valve means therebetween. The configuration further includes a communication passage to allow a closed space including the canister (formed when the purge control valve is closed) to communicate with the measurement passage on the side of one of the leading passages; another valve means for blocking the communication passage; and leakage determining means for determining leakage in the closed space based on values detected by the differential pressure detecting means in first and second leakage detection states. In the first leakage detection state, the measurement passage is not blocked and the communication passage is blocked. In the second leakage detection state, the measurement passage is blocked and the communication passage is not blocked.

In the second leakage detection state, the value detected by the differential pressure detecting means changes according to the size of a leak hole in the closed space. Information on the leakage in the closed space can be obtained by comparing the detected value to the value detected in the first leakage detection state in which the air is distributed through the orifice whose cross sectional area in the passage is a prescribed value. In this way, the volatility of the fuel or the concentration of the evaporated fuel in the purge gas can be measured without having to provide a complicated configuration. In addition, the detection for the fuel leakage can be carried out.

Still another aspect of the present invention includes engine operation state detecting means for detecting the operation state of the internal combustion engine, and the fuel nature is measured provided that the internal combustion engine is in a stopped state.

When the internal combustion engine is in a stopped state, the concentration of the evaporated fuel in the gas in the fuel tank is stable, and the fuel nature can be known more accurately.

According to yet another aspect of the present invention, the engine operation state detecting means detects whether an ignition key is on or off.

Whether the internal combustion engine is in a stopped state can easily be detected.

Still another aspect of the present invention includes fuel tank state detecting means for detecting change in the state caused by fueling to the fuel tank, and the fuel nature is measured in response to the fueling to the fuel tank.

By the fueling, the fuel tank is filled with fuel supplied by a different manufacturer and distributed in a different area from the previous one and therefore, it is highly likely that the volatility of the fuel before and after the fueling changes in a discontinued manner. Therefore, the fuel nature can be obtained more accurately.

According to still another aspect of the present invention, the fuel tank state detecting means detects whether a fuel cap of the fuel tank is open or closed.

The fuel tank in the process of being filled can easily be detected.

According to still another aspect of the present invention, the fuel tank state detecting means detects an amount of the fuel in the fuel tank and it is determined that the tank is in the process of being filled when the fuel amount is increased to a predetermined reference amount.

In this way, the fuel tank in the process of being filled can easily be detected.

According to still yet another aspect of the present invention, the fuel nature is measured for every prescribed time period.

The fuel stored in the fuel tank evaporates with time starting from its low boiling point component and therefore, the volatility is gradually lowered. Since the fuel nature is measured for every prescribed period, the change with time in the volatility is available.

According to still yet another aspect of the present invention, the temperature detecting means detects a temperature at a location other than the fuel tank, and estimates the temperature of the fuel based on the temperature detected at the location other than the fuel tank.

Other temperature detecting means provided at the internal combustion engine can also be used as the temperature detecting means. In this case, the temperature is detected at a sufficient time after the internal combustion engine stops, so that the concentration of the evaporated fuel in the fuel tank can be stabilized. Since the temperatures at various parts of the internal combustion engine converge to the ambient temperature, estimation errors can be reduced.

Yet still another aspect of the present invention includes an internal combustion engine having the fuel nature measuring device according to any of the aspects described above.

Since the amount of the fuel not contributing to the combustion in the combustion chamber can accurately be determined, the air-fuel ratio can be controlled appropriately.

An internal combustion engine according to yet another aspect of the present invention includes fuel injection amount setting means for setting a fuel injection amount at the start of the internal combustion engine based on the measured fuel nature.

Since the amount of fuel coming into the combustion chamber during cold starting can accurately be determined, the optimum fuel amount can be injected, and the internal combustion engine can be started quickly. In addition, excess fuel is not injected and therefore, the amount of fuel sticking to the internal wall or the like of the intake port can be reduced, which can reduce exhaust emission at the start of the engine.

Other features and advantages of the present invention will be appreciated, as well as methods of operation and the function of the related parts from a study of the following detailed description, appended claims, and drawings, all of which form a part of this application. In the drawings:

DETAILED DESCRIPTION OF THE PREFERRED EMBODIMENTS

Figure 1:
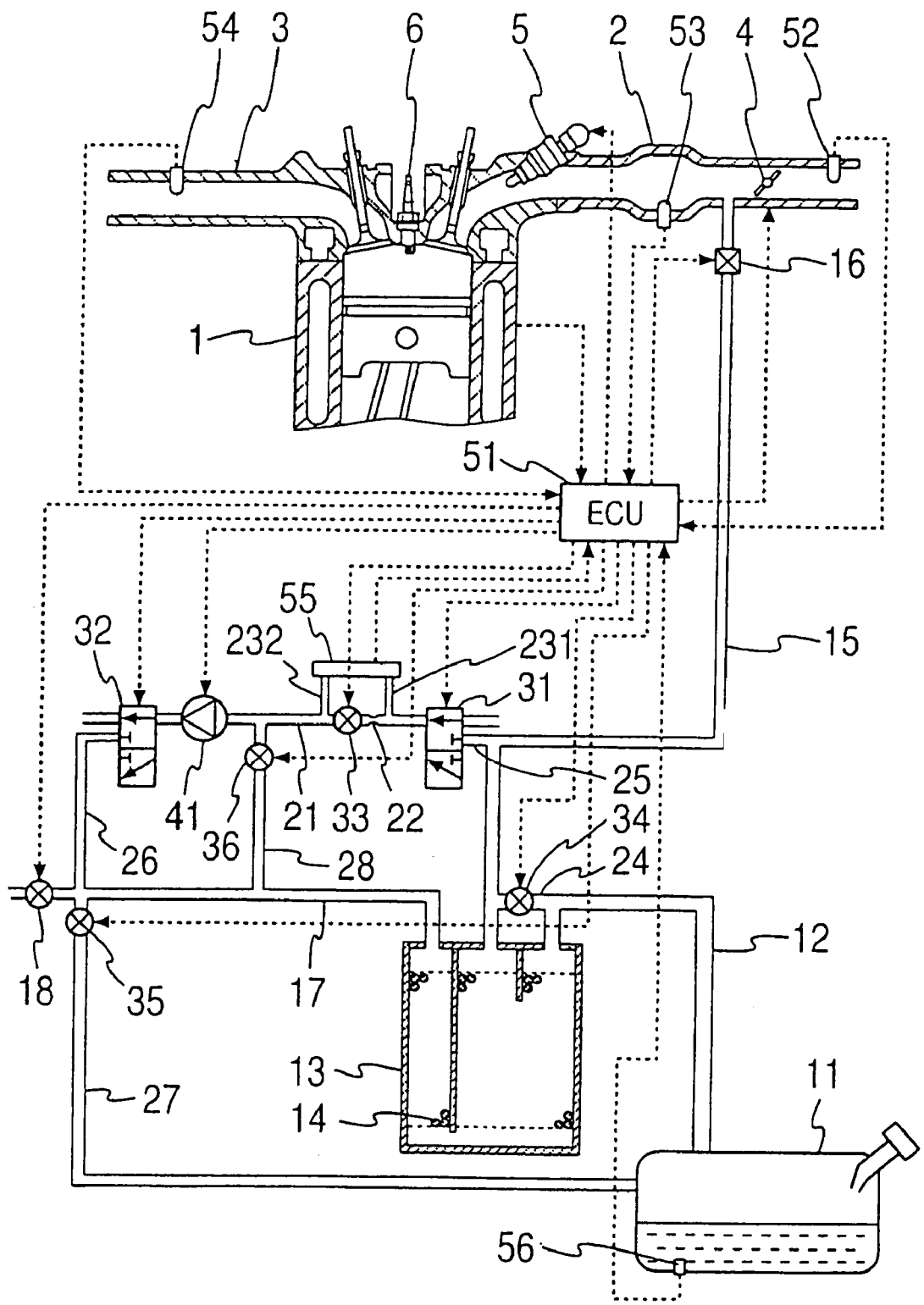
FIG. 1 is a schematic diagram of a fuel nature measuring device according to a first embodiment of the invention adapted to an internal combustion engine.

FIG. 1 illustrates a configuration of a fuel nature measuring device according to a first embodiment of the invention installed in an automobile engine. A fuel tank 11 for an internal combustion engine 1 is connected to a canister 13 through a conduit 12, and the fuel tank 11 and the canister 13 are continuously in communication. The canister 13 is filled with an absorbent 14 and the fuel evaporated in the fuel tank 11 is temporarily absorbed by the absorbent 14. The canister 13 is connected to an intake pipe 2 of the engine 1 through a purge passage 15. The purge passage 15 is provided with a purge valve 16 serving as a purge control valve, and when the valve opens, the canister 13 and the intake pipe 2 communicate.

The purge valve 16 is an electromagnetic valve and has its valve travel controlled by duty control or the like using an electronic control unit (ECU) 51 that controls various parts of the engine 1. Evaporated fuel desorbed from the absorbent 14 is purged into the intake pipe 2 by the negative pressure in the intake pipe 2 based on the valve travel and combusted together with fuel injected from an injector 5. Hereinafter, the air-fuel mixture including the evaporated fuel to be purged is referred to as "purge gas."

The canister 13 is connected to a purge air passage 17 that is open to the atmosphere at its tip end. The purge air passage 17 is provided with a close valve 18.

The purge passage 15 and the purge air passage 17 can be connected through an evaporated fuel passage 21, which serves as a measurement passage. The evaporated fuel passage 21 is connected to the purge passage 15 through a branch passage 25. The branch passage 25 communicates with the purge passage 15 at a point that is closer to the canister 13 than the purge valve 16. The evaporated fuel passage 21 is connected to the purge air passage 17 through a branch passage 26 that communicates with the purge air passage 17 at a point between the canister 13 and the close valve 18. The evaporated fuel passage 21 is provided with a first selector valve 31, an orifice 22, a valve 33, a pump 41, and a second selector valve 32 in this order from the side of the purge passage 15. The purge passage 15 can be connected to the conduit 12 through a communication passage 24 that communicates with the conduit 12 at a point closer to the canister 13 than the branch passage 25. The purge air passage 17 can be connected to the fuel tank 11 by a communication passage 27 at the branch portion to the branch passage 26. The communication passage 27 communicates with the fuel tank 11 above the level of the fuel regardless of the amount of fuel in the fuel tank 11 similar to the conduit 12. Communication passages 24 and 27 are provided with valves 34 and 35, respectively.

The purge air passage 17 and the evaporated fuel passage 21 communicate through a communication passage 28. One end of the communication passage 28 communicates with the evaporated fuel passage 21 at a point between the valve 33 and the pump 41, closer to the pump 41. The other end of the communication passage 28 communicates with the purge air passage 17 at a point between the canister 13 and the communication passage 26, closer to the communication passage 26.

The first selector valve 31 is a three-way electromagnetic valve that selects between first and second concentration measurement states. In the first concentration measurement state, the evaporated fuel passage 21 is opened to the atmosphere at one end, which is the right end in FIG. 1. In the second concentration measurement state, the evaporated fuel passage 21 communicates with the communication passage 25 at the end. The switching operation between the two states is controlled by the ECU 51. When the first selector valve 31 is in a non-conductive state (off), the first concentration measurement state is attained to let the evaporated fuel passage 21 open to the atmosphere.

The second selector valve 32 is also a three-way electromagnetic valve that selects between first and second concentration measurement states. In the first concentration measurement state, the evaporated fuel passage 21 is opened to the atmosphere at the other end, which is the left end if FIG. 1. In the second concentration measurement state, the evaporated fuel passage 21 communicates with the communication passage 26. The switching operation between the two states is controlled by the ECU 51. When the second selector valve 32 is in a non-conductive state (off), the first concentration measurement state is attained to let the evaporated fuel passage 21 open to the atmosphere.

The other valves 33, 34, 35, and 36 are two-way electromagnetic valves, and block the respective passages in which they are provided.

The pump 41, which serves as the gas flow generating means, is a motor pump that in operation allows gas to be distributed in and along the evaporated fuel passage 21 while the side of the first selector valve 31 serves as the intake side and has its on/off and revolution speed in operation controlled by the ECU 51. The revolution speed is controlled to be stable at a previously set value, in other words, fixed revolution speed control is carried out.

The evaporated fuel passage 21 is connected to a differential pressure sensor 55 serving as the differential pressure detecting means through connecting pipes 231 and 232 at the ends of the orifice 22 and the valve 33. The differential pressure sensor 55 detects the pressure difference between the ends of the orifice 22. A detection signal for the differential pressure is output to the ECU 51.

The fuel tank 11 is provided with a temperature sensor 56, which serves as the temperature detecting means, that detects the temperature inside the fuel tank 11. A detection signal for the temperature is output to the ECU 51.

The ECU 51 has a general configuration for an engine and includes a microcomputer as a main part. The ECU 51 controls elements such as a throttle 4 that is provided at the intake pipe 2 to adjust the intake air amount, an injector 5 that injects fuel, and an ignition plug 6 that ignites an air fuel mixture. This is carried out based on the amount of intake air detected by the air flow sensor 52 provided at the intake pipe 2, intake air pressure detected by an intake air pressure sensor 53, and an air-fuel ratio detected by an air-fuel ratio sensor 54 provided at an exhaust pipe 3 and in response to an ignition signal, the engine speed, the temperature of engine cooling water, the accelerator opening and the like. Accordingly, an appropriate throttle opening angle, a fuel injection amount, an ignition timing and the like can be obtained. Note that the pressure detected by the intake air pressure sensor 53 is given in absolute pressure, and equal to atmospheric pressure in the subsequent description of the fuel volatility calculation routine.

Figure 2:
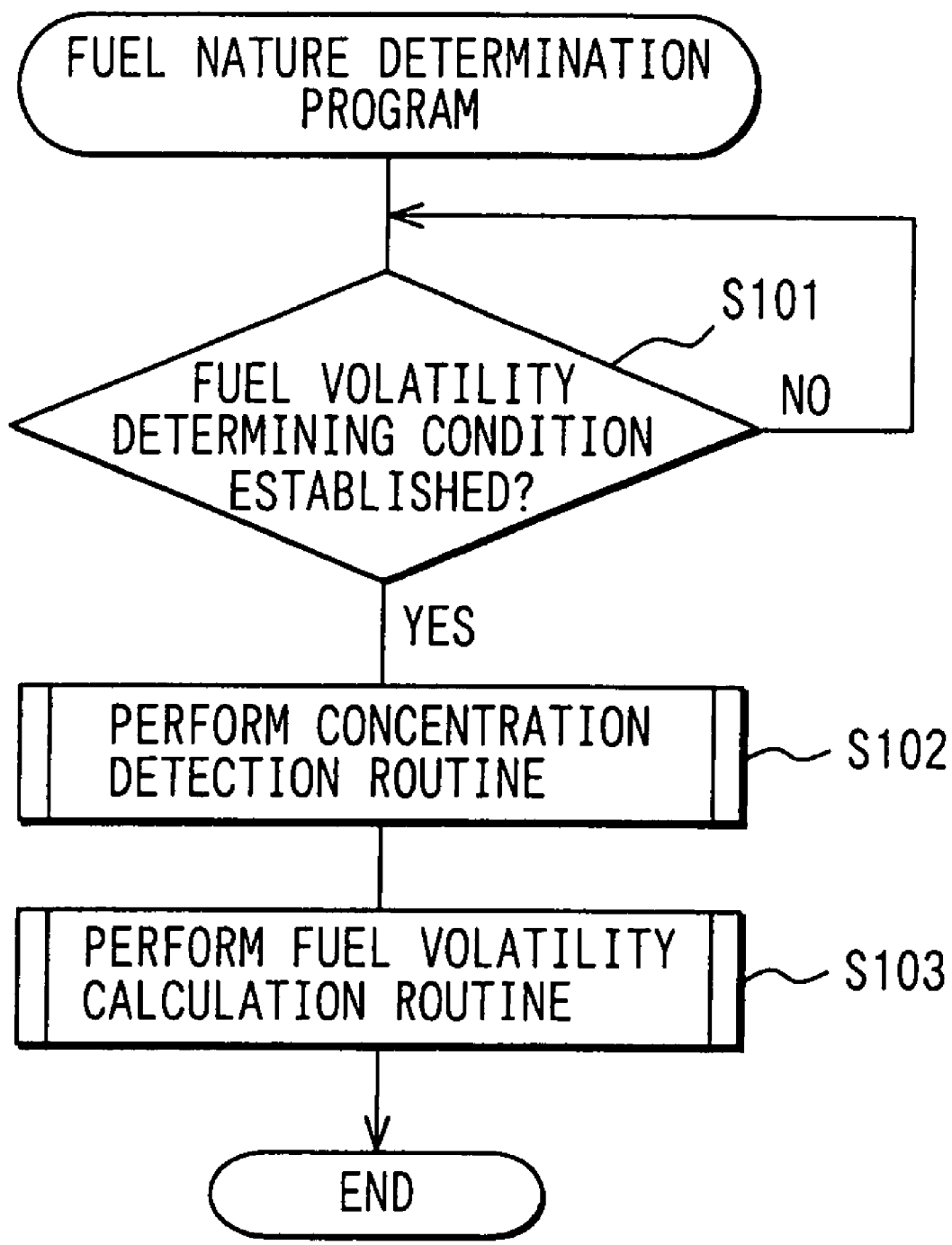
FIG. 2 is a flowchart of a fuel nature measuring process according to the first embodiment of the present invention.

FIG. 2 is a flowchart of the fuel nature determination process performed by the ECU 51 according to the principles of the first embodiment of the present invention. In step S101, it is determined whether a fuel volatility determining condition is established. The fuel volatility could change by fueling, or a passing of a prescribed time period or longer after the previous fueling or when the automobile having the engine is left unused for a long while in a high temperature environment and the low-boiling point component of the fuel in the fuel tank 11 is evaporated. The fuel volatility condition is so set that the volatility is to be determined when a change in the volatility is estimated for such a reason. The process of determining whether the fuel volatility determining condition is established will be described in more detail in connection with the subsequent third embodiment.

In general, when the result of the determination in step S101 is affirmative, the process proceeds to step S102 to carry out the concentration detection routine. When the result of the determination is negative, step S101 is repeated. After the concentration detection routine is performed at step S102, the fuel volatility calculation routine is performed in step S103.

Figure 3:
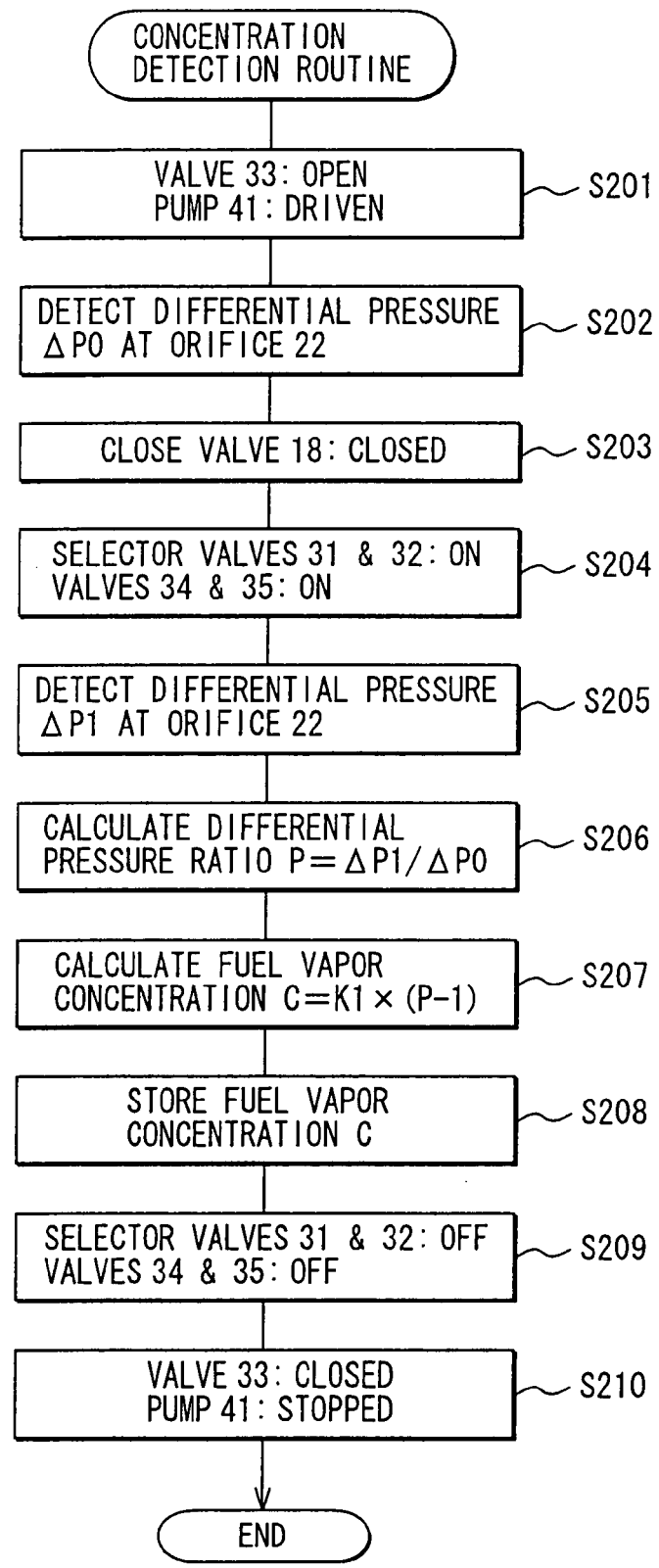
FIG. 3 is a second flowchart of a concentration detection routine of the fuel nature measuring process of FIG. 2.
Figure 4:
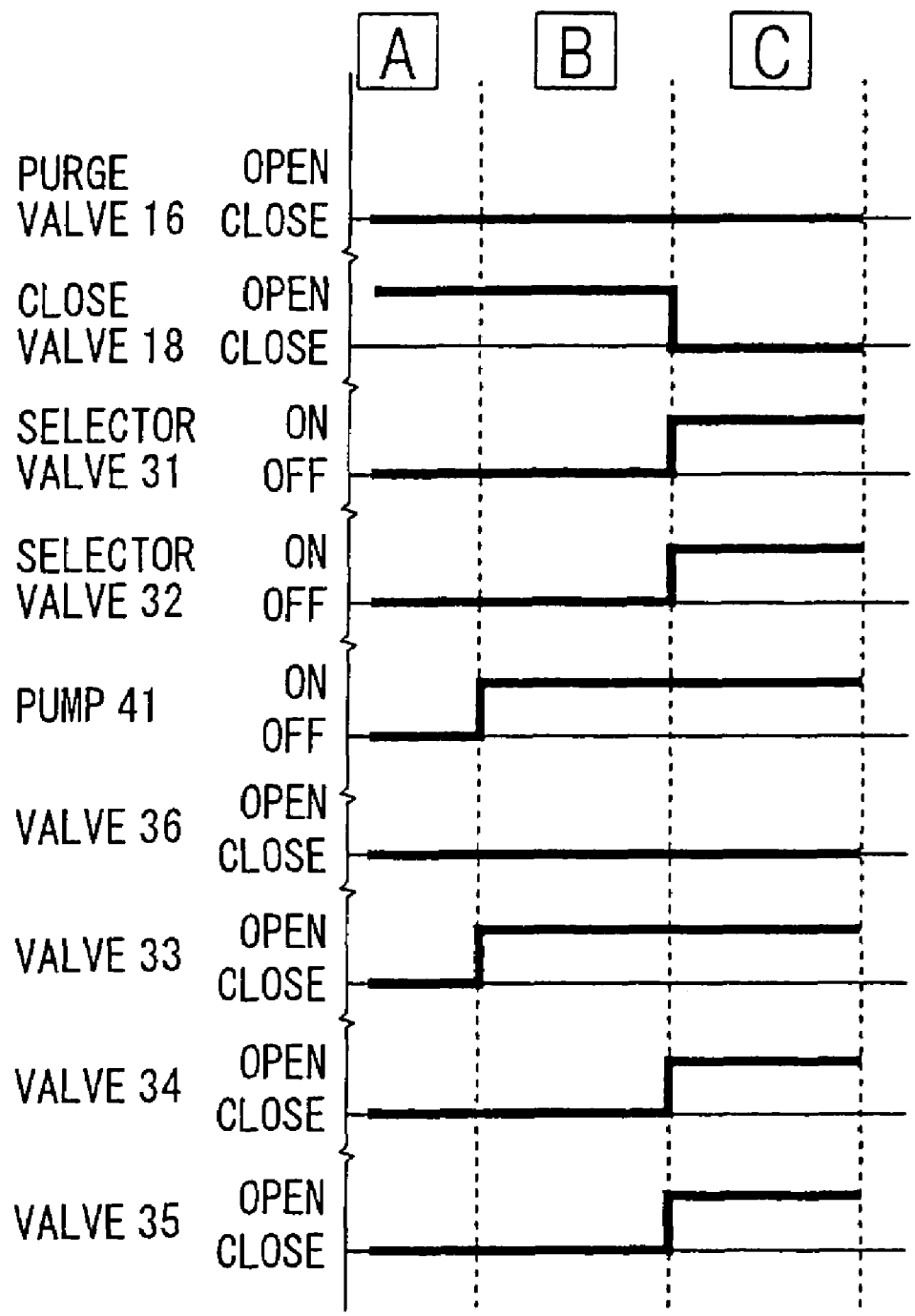
FIG. 4 is a timing chart illustrating various transitional states of various components of the fuel nature measuring device of FIG. 1 during the concentration detection routine of FIG. 3.
Figure 5:
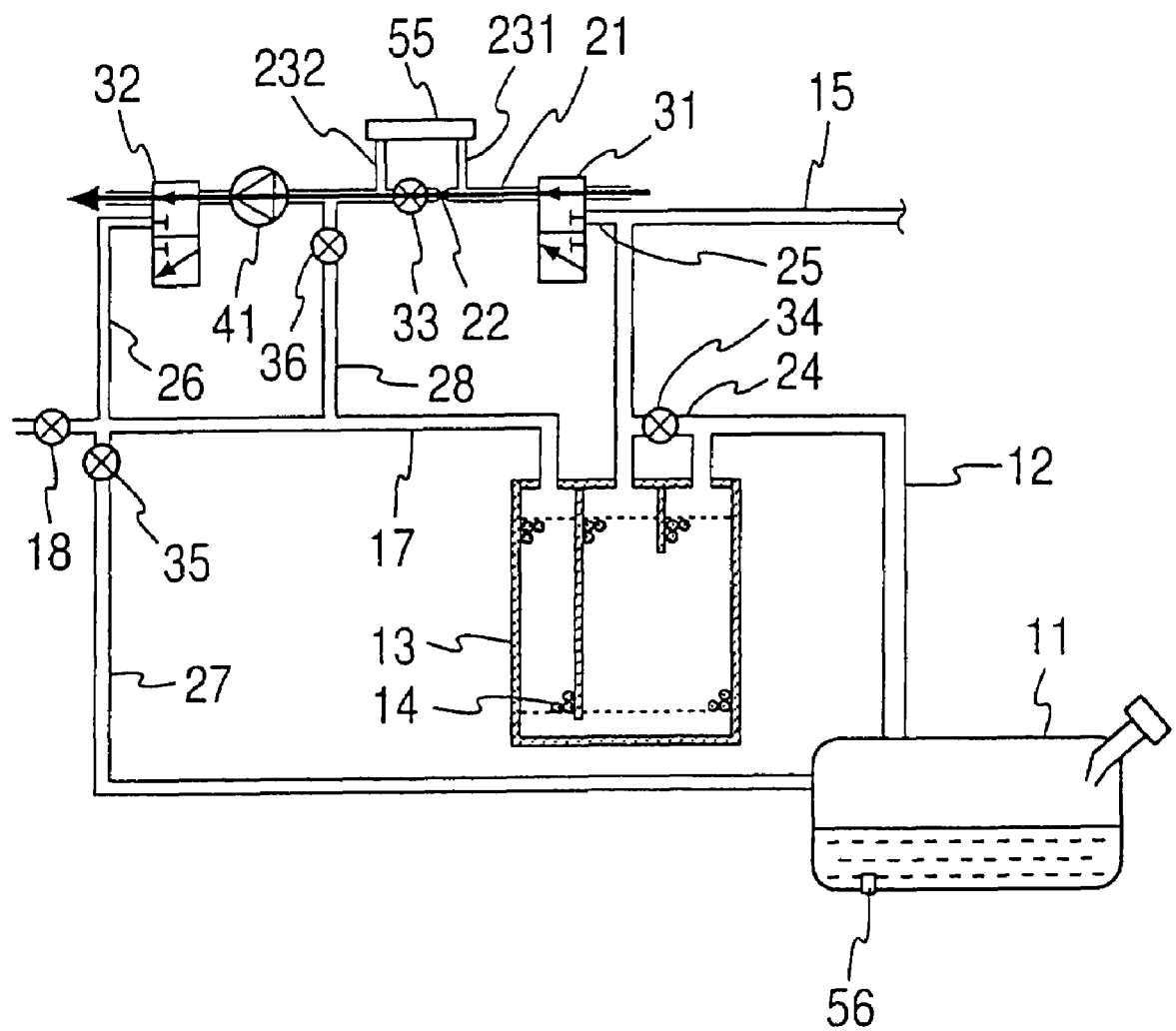
FIG. 5 is a top view of a part of the fuel nature measuring device of FIG. 1 in a first concentration measurement state.
Figure 6:
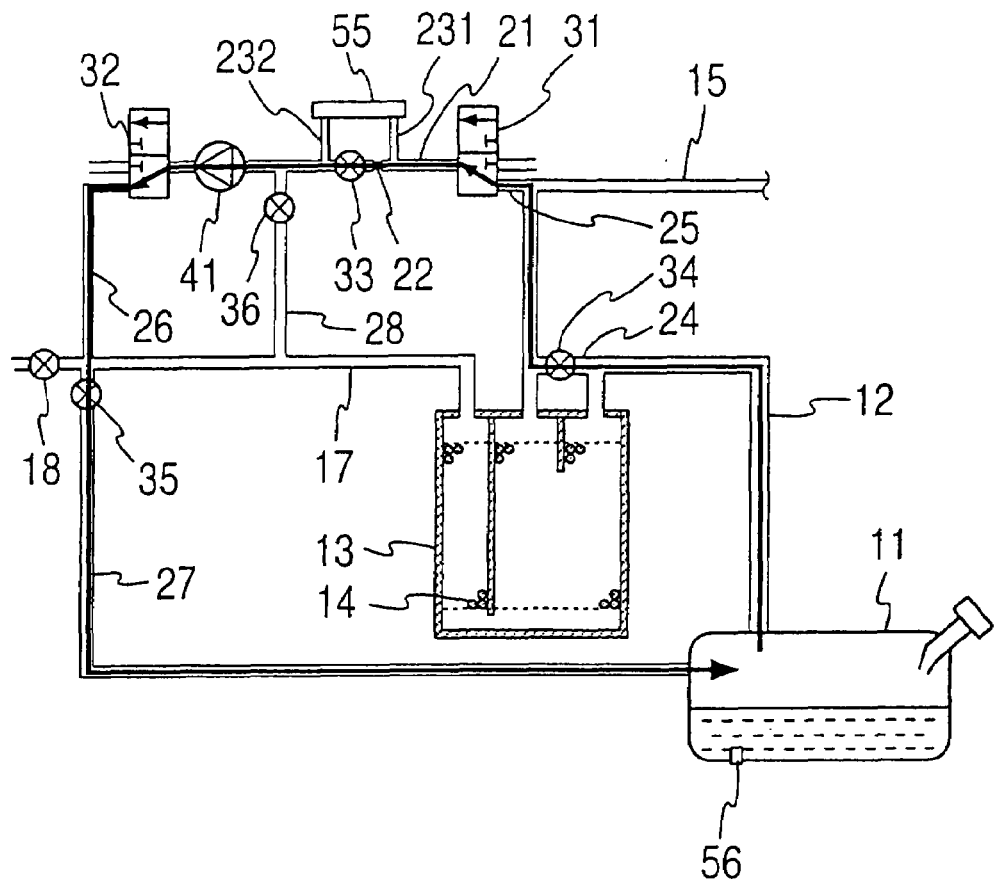
FIG. 6 is a top view of a part of the fuel nature measuring device of FIG. 1 in a second concentration measurement state.

FIG. 3 shows the content of the concentration detection routine performed in step S102 of FIG. 2. FIG. 4 shows the transition of the states of various parts of the device during the concentration detection routine. In the initial state in the concentration detection routine, the purge valve 16 is "closed" and the close valve 18 is "open." The first and second selector valves 31 and 32 are "off," in other words, the first concentration measurement state is attained, as depicted in FIG. 5. The valves 33 to 36 are closed or "off." The pump 41 is "off" (A in FIG. 4). In FIG. 3, in step S201, the valve 33 is opened to drive the pump 41, and gas is allowed to flow through the evaporated fuel passage 21 (B in FIG. 4). The gas is the air distributed through the evaporated fuel passage 21, as denoted by the arrow in FIG. 5, and returned into the atmosphere. In step S202, the differential pressure ΔP0 at the orifice 22 is detected. In step S203, the close valve 18 is closed and in step S204, the first and second selector valves 31 and 32 are turned on, while the valves 34 and 35 are opened (on)(C in FIG. 4). The state is therefore changed from the first concentration measurement state (shown in FIG. 5) to the second concentration measurement state (shown in FIG. 6). At this time, the purge valve 16 and the close valve 18 are closed and the valves 34 and 35 are open, so that the gas is circulated through a loop passage formed between the fuel tank 11 and the orifice 22, as shown in FIG. 6. The gas flow becomes an air-fuel mixture containing evaporated fuel as it is passed through the fuel tank 11.

In step S205, the differential pressure ΔP1 at the orifice 22 is detected.

The following steps S206 and S207 correspond to the process equivalent to the evaporated fuel concentration operation means, and the differential pressure ratio P is calculated in step S206 based on the obtained two differential pressures ΔP0 and ΔP1 according to expression (1) provided below. In step S207, the fuel vapor concentration C is calculated based on the differential pressure ratio P according to expression (2) provided below, wherein k1 represents a constant pre-stored in the ROM of the ECU 51 together with a control program and other programs.

$$P = \Delta P1/\Delta P0 \tag{1}$$

$$C = k1 \times (P-1)(= .(\Delta P1 - \Delta P0)/\Delta P0) \tag{2}$$

Figure 7:
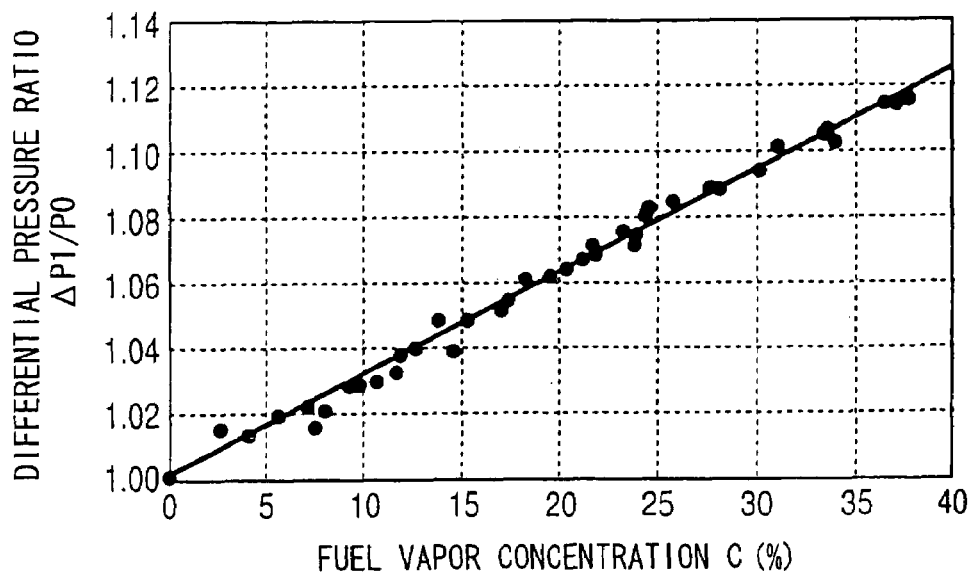
FIG. 7 is a first graph illustrating the operation of the internal combustion engine according to the first embodiment of the present invention illustrating gas flow.

The evaporated fuel is heavier than the air and therefore, if the gas from the fuel tank 11 contains the evaporated fuel, the density of the gas increases. For the same revolution speed and the same flow rate in the evaporated fuel passage 21, the differential pressure at the orifice 22 is larger than the air based on the energy conservation law. As the fuel vapor concentration C increases, the differential pressure P increases. The characteristic line representing the fuel vapor concentration C and the differential pressure P is linear, as shown in FIG. 7. Expression (2) provided above represents the characteristic line and the constant k1 is previously obtained from experiments and the like.

In the first concentration measurement state, which is shown in FIG. 5, air distributes through the evaporated fuel passage 21 and the fuel vapor concentration is zero. Here, the differential pressure about the gas with known concentration and the differential pressure in the second concentration measurement state to allow the gas in the fuel tank 11 to be distributed in the evaporated fuel passage 21 are detected, so that detection errors can be cancelled, which results in highly precise detection.

In step S208, the obtained fuel vapor concentration C is temporarily stored.

The first and second selector valves 31 and 32 are turned off, and the valves 34 and 35 are closed (off) in step S209, the valve 33 is closed (off) in step S210, and the pump 41 is turned off. The state is the same as the state denoted by A in FIG. 4, in other words, the state before the start of the concentration detection routine is regained.

Figure 8:
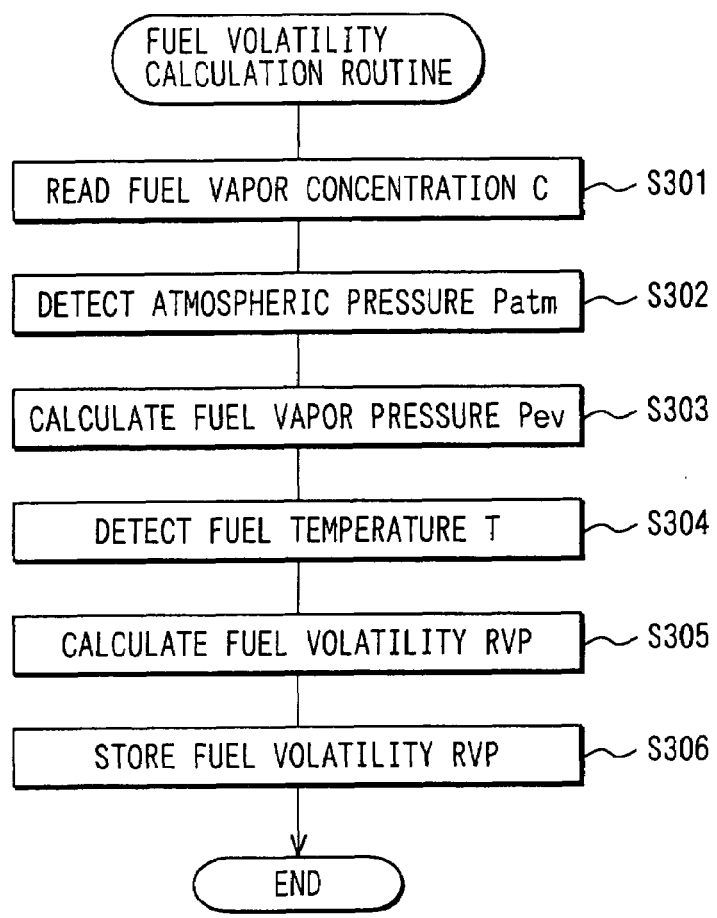
FIG. 8 is a flowchart of a fuel volatility calculation routine of the fuel nature measuring process of FIG. 2.

FIG. 8 shows the fuel volatility calculation routine of step S103 of FIG. 2. First, in step S301 of FIG. 8, the fuel vapor concentration C obtained in the concentration routine is read.

In step S302, atmospheric pressure Patm is detected. The atmospheric pressure Patm is detected by the intake air pressure sensor 53.

In step S303, fuel vapor pressure Pev is calculated according to expression (3) provided below. Expression (3) is based on the fact that the concentration of the evaporated fuel is the ratio of the saturated vapor pressure of the fuel to the atmospheric pressure.

$$Pev = Patm \times C \qquad (3)$$

In step S304, the fuel temperature T is detected.

Figure 9:
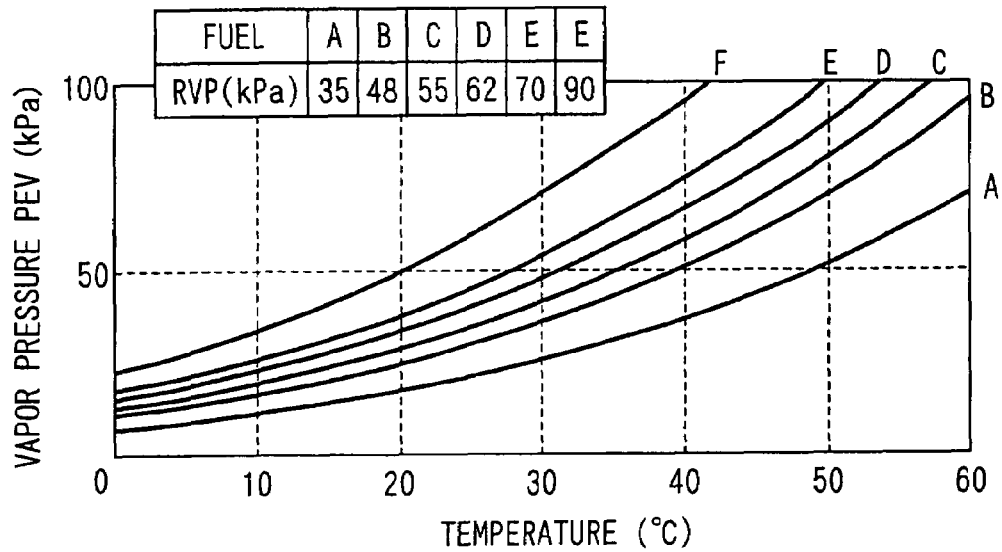
FIG. 9 is a reference map for use in the fuel volatility calculation routine of FIG. 8.

The following step S305 is equivalent to the process performed by the volatility calculation means, and read vapor pressure RVP is calculated as the fuel volatility based on the fuel vapor pressure Pev and the fuel temperature T. As shown in FIG. 9, the ECU 51 stores the characteristic line between the temperature T and the vapor pressure Pev in the form of a map. The fuel volatility RVP is calculated referring to the map. The obtained fuel volatility RVP is temporarily stored in a memory in step S306.

Figure 10:
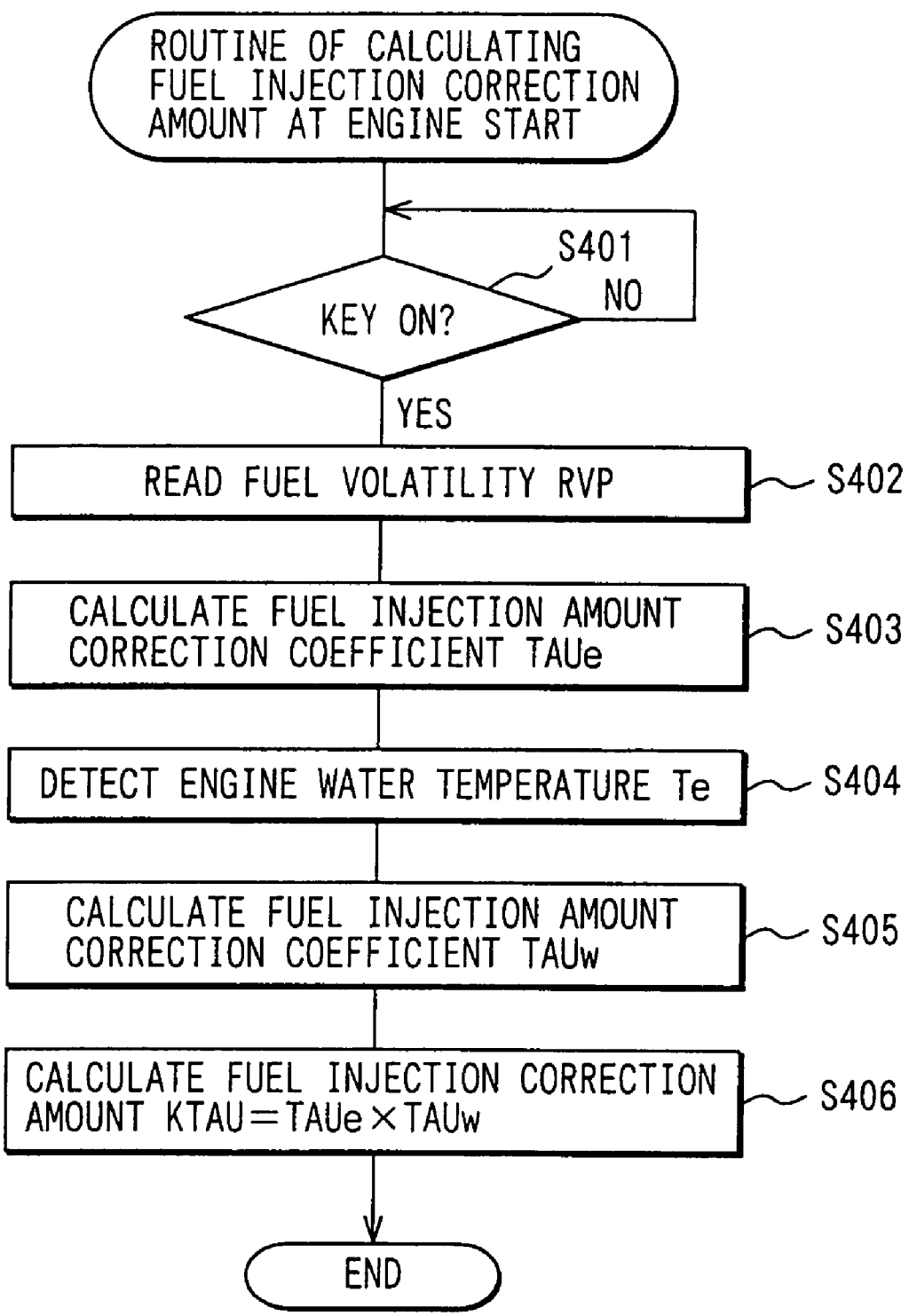
FIG. 10 is a fourth flowchart of a fuel injection correction amount routine according to the first embodiment of the present invention.

Now, referring to FIG. 10, the routine of calculating a fuel injection correction amount at the start will be described. It is determined in step S401 whether the ignition key is turned on, and if the result of this determination is affirmative, the process proceeds to step S402. If the result is negative, step S401 is repeated.

Steps S402 to S406 are equivalent to the process carried out by the correction amount setting means, and in step S402, the fuel volatility RVP obtained in the fuel volatility calculation routine is read. In step S403, the fuel injection amount correction coefficient TAUe corresponding to the fuel volatility RVP is calculated. The calculation is carried out according to a map or the like in which the fuel volatility RVP and the fuel injection amount correction coefficient TAUe are associated with each other.

In step S404, the engine water temperature Tw is detected and a fuel injection correction coefficient TAUw according to the engine water temperature Tw is calculated in step S405. The calculation is carried out according to a map or the like in which the engine water temperature Tw and the fuel injection amount correction coefficient TAUw are associated with each other.

In step S406, the fuel injection correction amount KTAU is calculated according to expression (4) provided below. The fuel injection correction amount KTAU is multiplied by the injection amount TAU calculated based on the throttle opening angle and the engine speed to produce the final injection amount.

$$KTAU = TAUe \times TAUw \qquad (4)$$

The map for producing the fuel injection amount correction coefficient TAUe is set so that as the fuel volatility RVP increases, the coefficient not less than 1 decreases toward 1. This is because there is little likelihood that injected fuel with high fuel volatility RVP sticks and does not contribute to combustion.

The map for producing the fuel injection amount correction coefficient TAUw is set so that as the engine water temperature Tw increases, the coefficient not less than 1 decreases toward 1. This is because when the engine water temperature Tw is high, the temperature of the intake pipe 2 is high, which makes easier the evaporation, so that there is little likelihood that injected fuel sticks and does not contribute to combustion.

In this way, the fuel injection amount is appropriately adjusted according to the volatility of the fuel, so that the air-fuel ratio can be controlled highly precisely.

Since the concentration of the evaporated fuel in the gas passing through the fuel tank 11 can be detected, the ECU 51 forms other evaporated fuel operation means at the evaporated fuel passage 21. The operation means calculates the concentration of the evaporated fuel in the purge gas as follows. The valves 34 and 35 are closed based on the second concentration measurement state, so that the gas in the canister 13 is circulated between the canister 13 and the evaporated fuel passage 21. Then, based on the differential pressure at the orifice 22 at the time, the concentration of the evaporated fuel in the purge gas is calculated. The concentration detection routine is substantially the same as the content shown in FIG. 3 except for how the valves 34 and 35 are set. More specifically, the concentration of the evaporated fuel in the purge gas is available based on the differential pressure ratio of the differential pressures at the orifice 22 when the air is passed through the evaporated fuel passage 21 and when the purge gas as the gas for measurement is passed through the evaporated fuel passage 21.

In this way, the valve travel of the purge valve 16 can be set to an appropriate value, and the amount of the evaporated fuel in the purge gas can appropriately be adjusted.

The ECU 51 also forms the leakage determining means for checking leakage in a simple manner using an evaporator system as a detection space for leakage. The evaporator system defines a closed space from the fuel tank 11 through the canister 13 to the purge valve 16 in which the evaporated fuel is present while the purge valve 16 is closed. More specifically, the first and second selector valves 31 and 32 are off, the valve 33 as the valve means is opened, and the valve 36 as other valve means is closed. This defines the first leakage detection state. In this state, the pump 41 is driven, and the differential pressure detected by the differential pressure sensor 55 is obtained at prescribed intervals. The detection output represents the pressure in the evaporated fuel passage 21 toward the side of the pump 41 relative to the atmospheric pressure as the reference and gradually increases to the negative side as the pump 41 starts to be driven. When the differential pressure between the detected pressure and the previous value is not more than a predetermined reference value, the detection output (reference pressure) at the time is stored.

Then, valve 33 is closed, valve 36 is opened, and the close valve 18 is closed. This defines a the second leakage detection state. The pump 41 is driven in the state. Similarly, the differential pressure detected by the differential pressure sensor 55 is obtained at prescribed intervals. The detection output is a pressure in the evaporator system relative to the atmospheric pressure and serves as a reference. When the differential pressure between the detected pressure and the previous value is not more than the reference value, the detection output at the time is stored and compared to the reference pressure. When the evaporator system has a hole having an area as large as the orifice 22, a pressure value equal to the reference pressure is obtained. When the evaporator system has a hole having an area larger than the orifice 22, the detected pressure is smaller. Therefore, if the pressure is greater than the reference pressure value, it is determined that there is no leakage in the evaporator system. Otherwise it is determined that there is leakage.

Note that the difference between the detection output and the previous value, in other words, the amount of change must be at most the reference value in order to allow the detection pressure to converge.

In this way, as the air and the gas for measurement are distributed in the evaporated fuel passage having the orifice, not only the volatility of the fuel, but also the concentration of the evaporated fuel in the purge gas can be obtained. In addition, the evaporator system can be checked for leakage. Therefore, such a multi-function device can be implemented with low cost.

Figure 11:
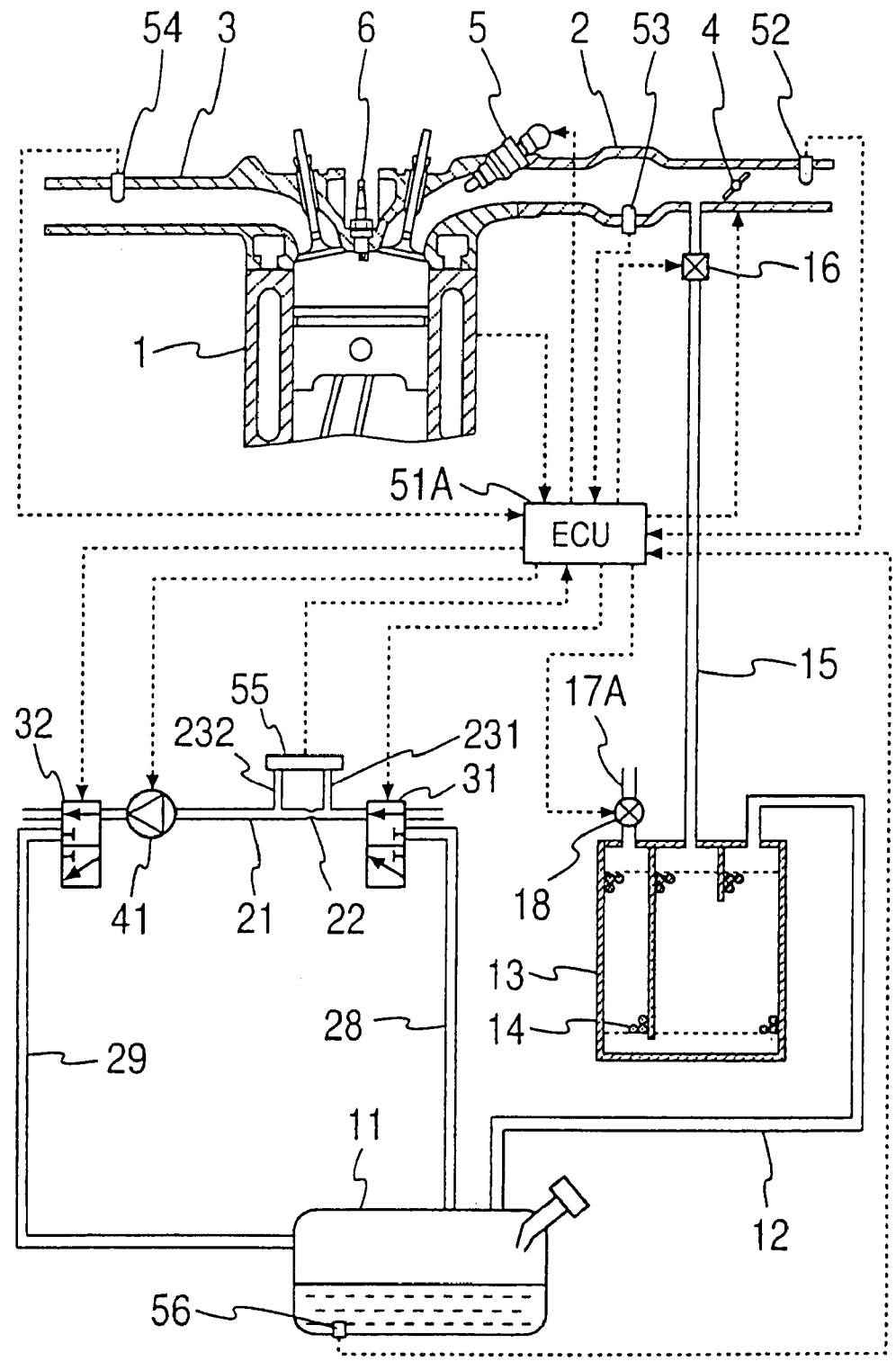
FIG. 11 is a schematic diagram of a fuel nature measuring device according to a second embodiment of the present invention.

FIG. 11 shows a fuel nature measuring device according to the principles of a second embodiment of the present invention. The second embodiment is substantially the same as the first embodiment with except that a part of the configuration. The elements of the second embodiment that ate substantially the same as those of the first embodiment are denoted by the same reference characters, while the different elements will mainly be described.

A purge air passage 17A is a simple passage unconnected to other conduits and closed by a close valve 18 provided therein.

An evaporated fuel passage 21 is provided with selector valves 31 and 32 at the ends similarly to the first embodiment. When the selector valves 31 and 32 are on, the evaporated fuel passage 21 communicates with the fuel tank 11 on one side, through a communication passage 28, and, on the other side, through a communication passage 29.

Similar to the first embodiment, an ECU 51A can calculate the fuel volatility RVP by detecting the differential pressures at the orifice 22. In a first measurement state, the ECU 51A turns off the selector valves 31 and 32 to cause air to enter into the evaporated fuel passage 21. In a second measurement state, the ECU 51A turns on the selector valves 31 and 32 to distribute gas containing evaporated fuel from the fuel tank 11 into the evaporated fuel passage 21.

Figure 12:
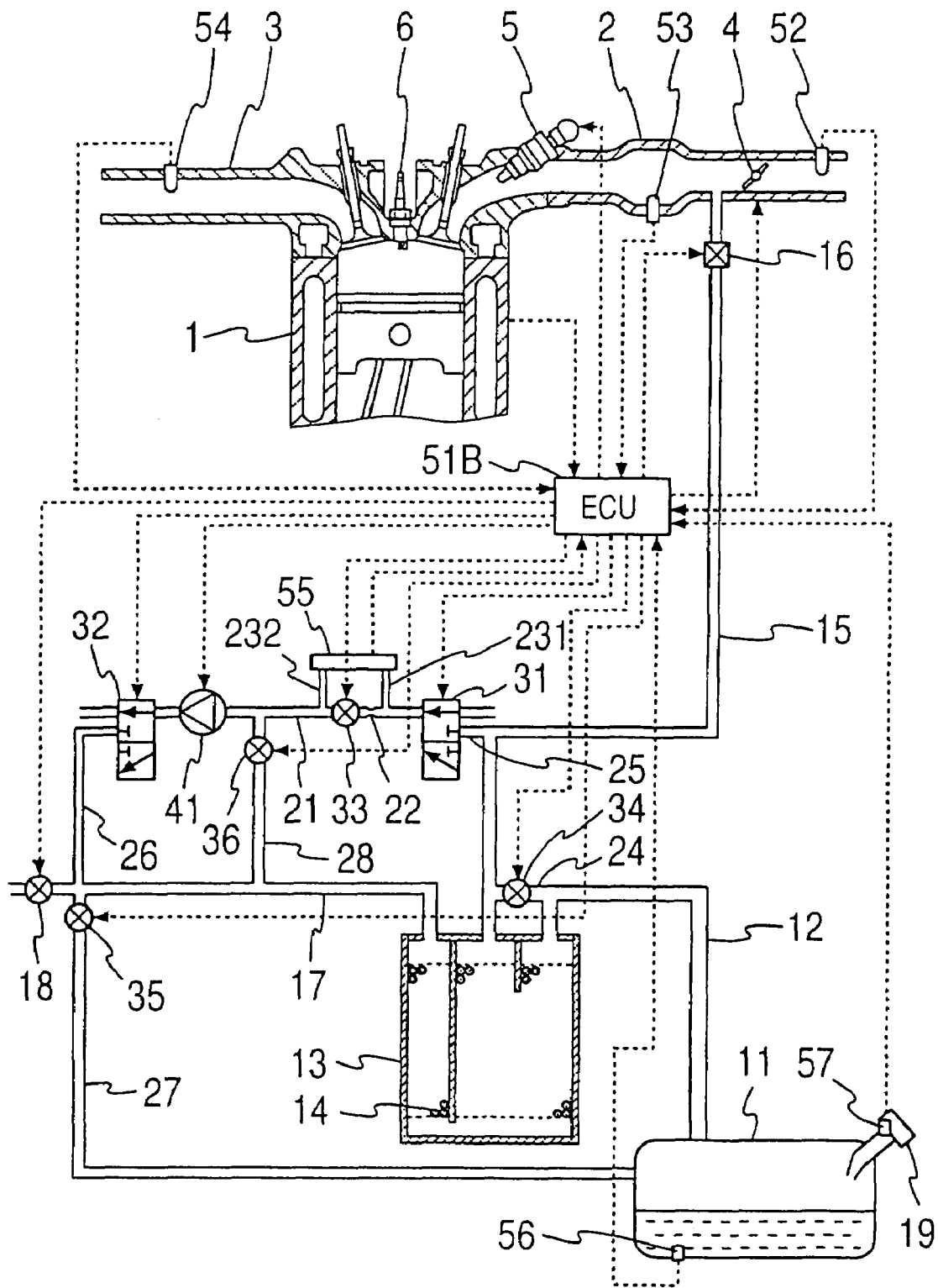
FIG. 12 is a schematic diagram of a fuel nature measuring device according to a third embodiment of the present invention.

FIG. 12 shows a fuel nature measuring device according to the principles of a third embodiment of the present invention. The third embodiment is substantially the same as the first embodiment except for a part of the configuration. The elements of the third embodiment that are substantially the same as those of the first embodiment are denoted by the same reference characters, while the different elements will mainly be described.

A fuel cap 19 at the fuel inlet of the fuel tank 11 has its open/closed state detected by a sensor 57, which serves as the fuel tank state detecting means, so that the open/closed state of the fuel cap 19 is available to an ECU 51B. The sensor 57 may be a switch type sensor, an optical type sensor, a capacitance type sensor, or any of various other kinds of sensors.

Figure 13:
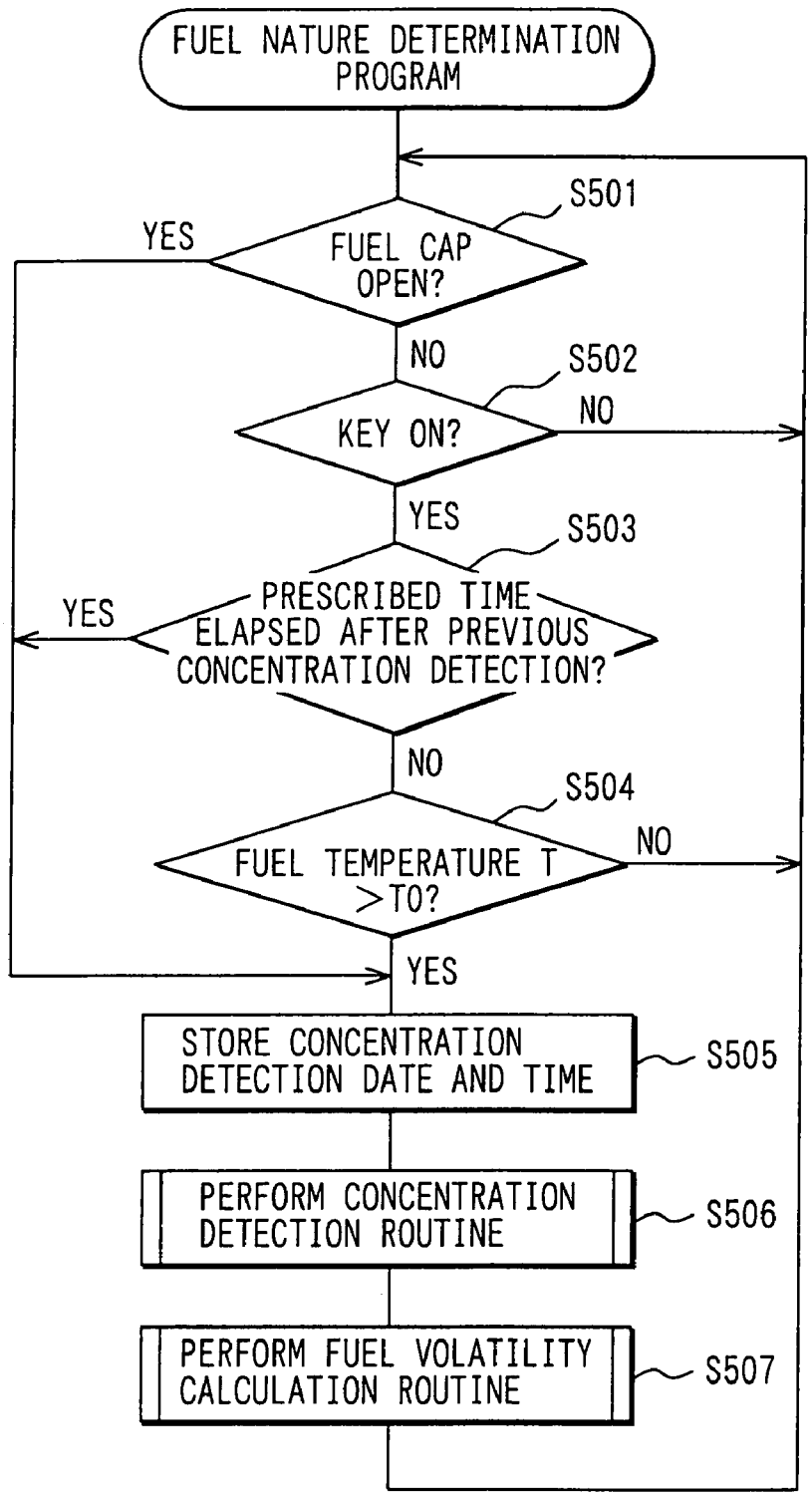
FIG. 13 is a flowchart of a fuel nature measuring process according to the third embodiment of the present invention.

FIG. 13 partly shows how control is carried out by the ECU 51 B of the third embodiment of the present invention. It is determined in step S501 whether or not the fuel cap 19 is "open." If the result of determination is affirmative, the present time is stored in step S505 as the concentration detection date and time. In the following step S506, the concentration detection routine is performed. In step S507, the fuel volatility calculation routine is performed. These concentration detection routine and fuel volatility calculation routine are performed similar to those of the first embodiment. After the fuel volatility calculation routine is performed at step S507, the process returns to step S501.

When the result of determination is negative in step S501, it is determined in step S502 whether the ignition key is in an "on" state. If the result of determination is negative, the process returns to step S501. The concentration detection routine at step S506 and the fuel volatility calculation routine at step S507 are not performed.

When the result of determination in step S502 is affirmative, it is determined in step S503 whether a prescribed time period has elapsed after the previous concentration detection. This is determined based on the stored concentration detection date and time from step S505. If the result of determination is affirmative, the process from steps S505 to S507 is performed. Therefore, during the period before the next fueling, the volatility of the fuel is determined at intervals of the prescribed time period. The evaporation of the low boiling point component in fuel proceeds with time, which changes the volatility of the fuel and therefore, the fuel injection amount is adjusted appropriately in response to the change in the volatility.

If the result of determination is negative in step S503, it is determined in step S504 whether the fuel temperature T is greater than the prescribed temperature T0. If the result of determination is affirmative, the process from steps S505 to S507 is performed. At the higher fuel temperatures T, the low boiling point component in combustion evaporates more easily, and the volatility of the fuel changes more rapidly. Therefore, if the prescribed time period has not elapsed after the previous concentration detection, it is highly likely that there is a significant change in the volatility. The fuel injection amount can be adjusted appropriately in response to the change in the volatility.

If the result of determination in step S504 is negative, the process returns to step S501.

In this way, the fuel nature is determined in the timing when some significant change in the fuel nature is recognized, and the operation frequencies of the pump 41, the selector valves 31 and 32, and valves 33 to 35 can be lowered to reduce the power consumption from the batteries. This can also alleviate the calculation load.

Note that if the elapsed time after the previous concentration detection is greater than or equal to the prescribed time period, the ignition key must be on even at a temperature that is greater than or equal to the prescribed temperature T0. This is because the fuel is not injected during the ignition-off period, the result of fuel nature measuring process is not used for controlling the engine, and the power can be saved during the period. However, if the power consumption can be ignored, the operation may be carried out during the ignition-off period as will be described below in the fifth embodiment.

Figure 14:
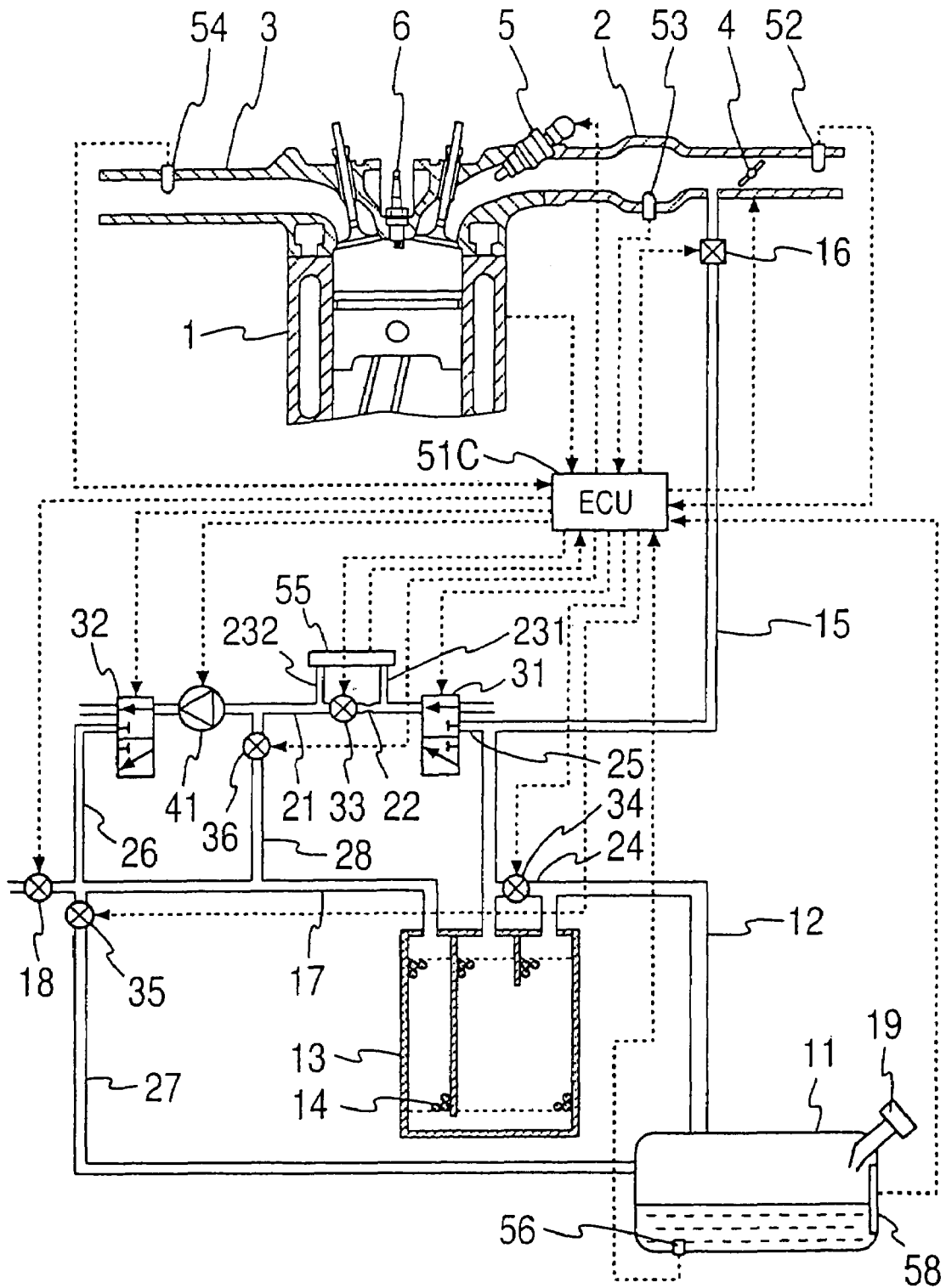
FIG. 14 is a schematic view of a fuel nature measuring device according to a fourth embodiment of the present invention adapted to an internal combustion engine.

FIG. 14 shows a fuel nature measuring device according to a fourth embodiment of the present invention. The fourth embodiment is substantially the same as the first embodiment except for a part of the configuration. The elements of the fourth embodiment that are substantially the same as those of the first embodiment are denoted by the same reference characters, while the different elements will mainly be described.

A fuel level gauge 58, which serves as the fuel tank state detecting means for detecting the fuel amount, is provided in the fuel tank 11. The fuel level gauge 58 may be a float type device or any of other kinds of detecting devices. A detection signal from the fuel level gauge 58 is input to an ECU 51C, so that the fuel amount is available.

Figure 15:
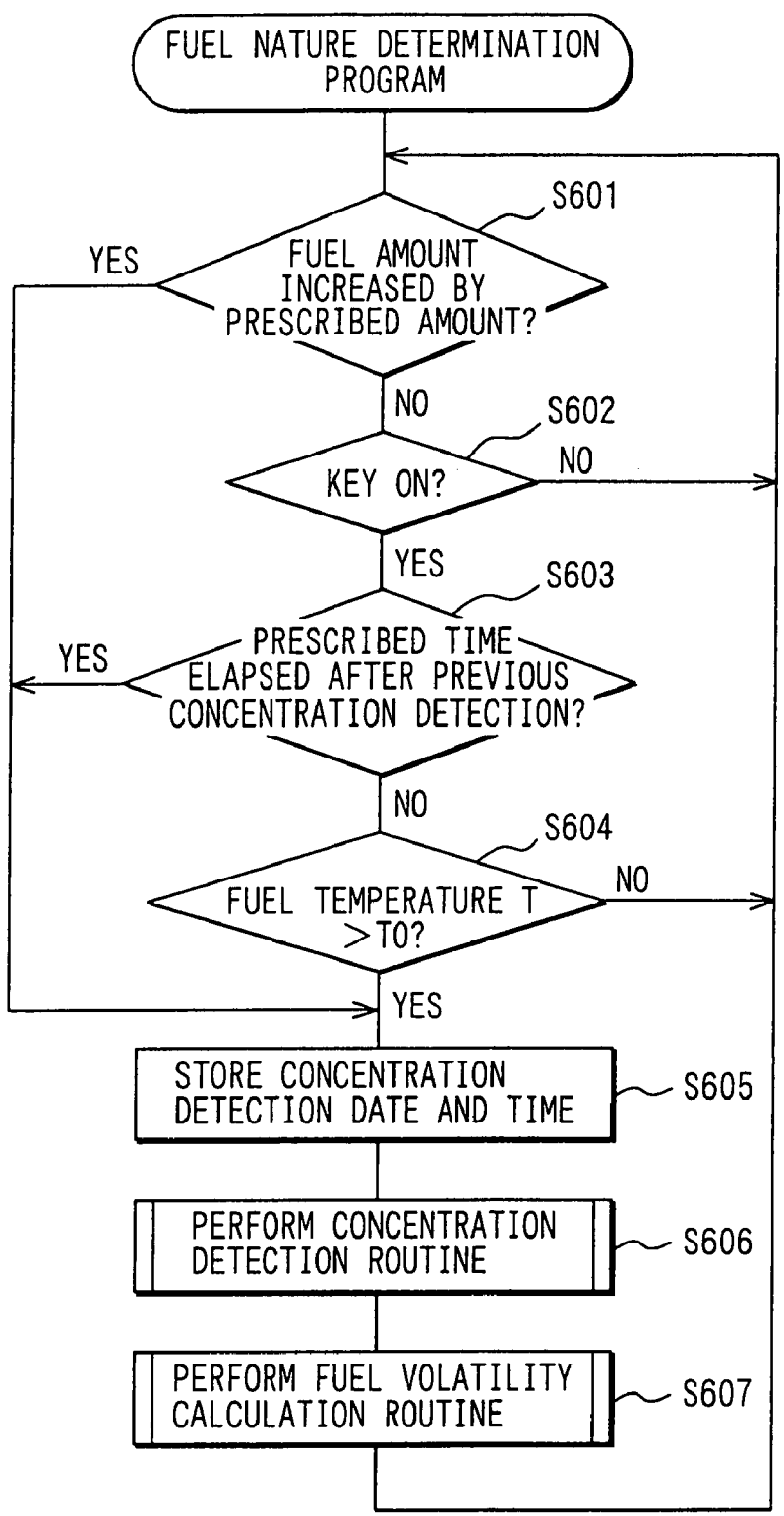
FIG. 15 is a flowchart of a fuel nature measuring process according to the fourth embodiment of the present invention.

FIG. 15 shows a part of the control carried out by the ECU 51C of the fourth embodiment. It is determined in step S601 whether the fuel amount has increased by a prescribed amount or more. If the result of determination is affirmative, steps S605 to S607 are performed. In steps S605 to S607 that are the same as the process from steps S505 to S507, the present date and time are stored as concentration detection date and time (step S605), the concentration detection routine is performed (step S606), and the fuel volatility calculation routine is performed (step S607). The fuel in the fuel tank 11 increases at the time of fueling, and the occurrence of fueling can be detected in the same manner as in step S501 according to the third embodiment. If the result of determining whether the fuel amount increase is greater than or equal to the prescribed amount, in step S601, is negative, the process proceeds to step S602. Steps S602 to S604 are the same as the process from steps S502 to S504 according to the third embodiment. If the ignition key is "on" (step S602) and the prescribed time has passed after the previous concentration detection (step S603), or if the fuel temperature T attains the prescribed temperature T0 or higher, the process of determining the fuel nature is performed (steps S605 to S607).

Note that the prescribed amount compared to the fuel amount in step S601 must be set to a sufficiently large value, such that the appearance of a fuel increase due to the vehicle being parked on a slope is not mistaken for a fuel amount increase. The fueling is generally carried out when the fuel amount is reduced to half the full tank level and therefore, it is easy to set the prescribed value to a level that cannot allow such mistaken determination.

Figure 16:
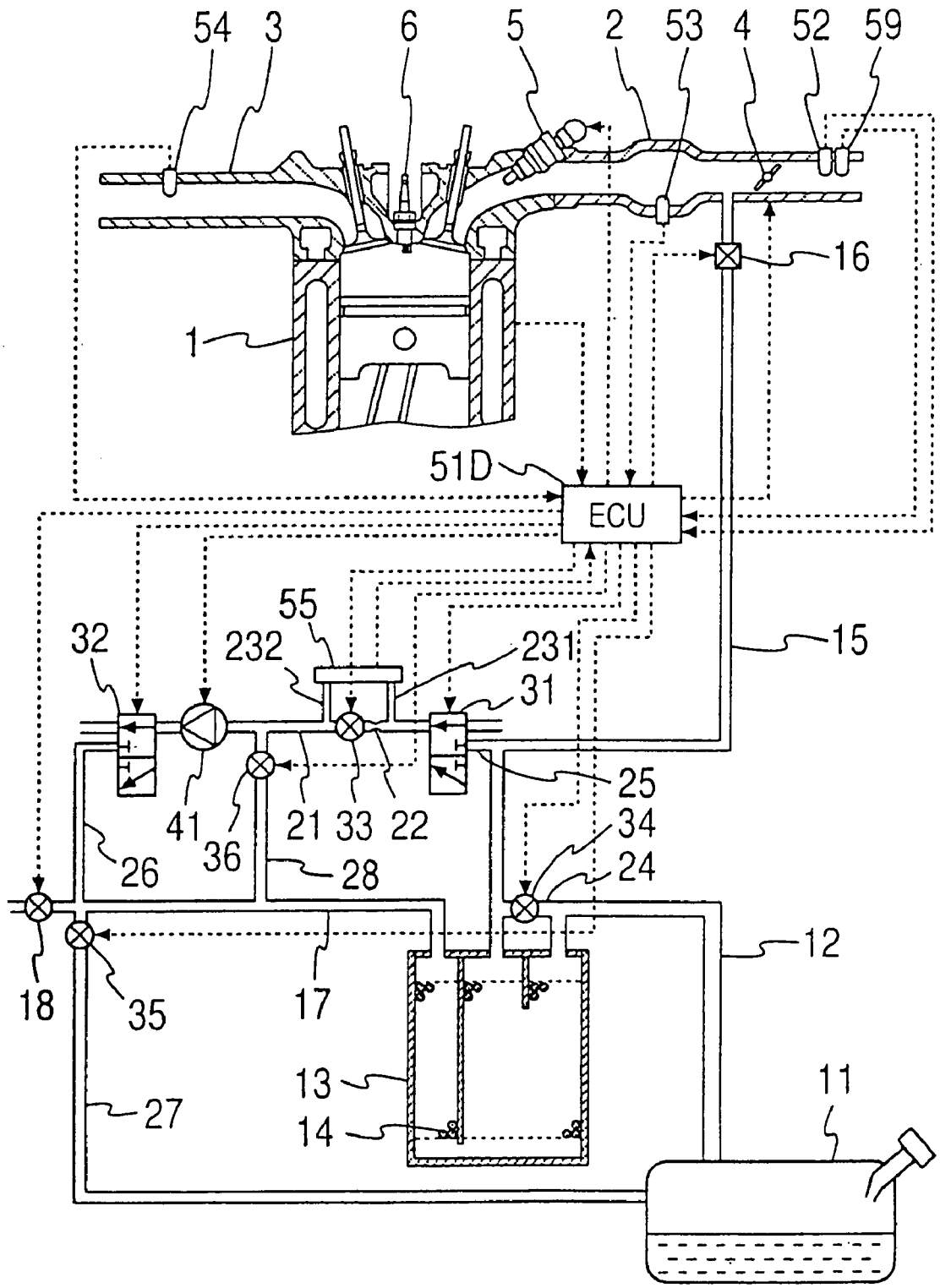
FIG. 16 is a schematic diagram of a fuel nature measuring device according to a fifth embodiment of the present invention adapted to an internal combustion engine.

FIG. 16 shows a fuel nature measuring device according to the principles of a fifth embodiment of the present invention. The fifth embodiment is substantially the same as the first embodiment except for a part of the configuration. The elements of the fifth embodiment that are substantially the same as those of the first embodiment are denoted by the same reference characters, while the different elements will mainly be described.

An air flow sensor 52 in an intake pipe 2 has an intake air temperature sensor 59 that detects the temperature of intake air. The intake air temperature sensor 59 is formed as a unit in the air flow sensor 52. A detection signal from the intake air sensor 59 is input to an ECU 51 D, so that the intake air temperature is available to the ECU 51 D.

The ECU 51 D performs control substantially the same as that by the ECU 51 according to the first embodiment, and the intake temperature sensor 59 is substituted for the temperature sensor 56 of the first embodiment. More specifically, immediately after the ignition key is turned "off," the fuel tank 11 is approximately at the ambient temperature, while the intake pipe 2 provided in the engine room is at a high temperature. Then, the temperature of the intake pipe 2 converges toward to the ambient temperature after a sufficient period of time.

Therefore, after the elapse of a prescribed time period after the ignition key is turned "off," the temperature detected by the intake temperature sensor 59 is considered substantially equal to the temperature of the fuel. Then, the concentration detection routine and the fuel volatility measuring routine are performed in the same manner as the first embodiment, so that the fuel nature can be determined. Note that the prescribed time period is, for example, a 5-hour period, in which the temperature of the intake pipe 2 is recognized to have converged to the ambient temperature. The convergence characteristic of the temperature of the intake pipe 2 may be obtained from experiments and the prescribed time period may be set based on the result. Therefore, it should be appreciated that the prescribed time period can be any time period less than or greater than 5 hours.

The use of the intake air temperature sensor 59 provided at the airflow sensor 52 simplifies the configuration. Any temperature detecting means provided in the vehicle having the engine may be used but the use of the intake air temperature sensor 59 is preferable because fresh air is distributed in the intake air passage 2 and therefore, the detected temperature is basically close to the temperature inside the fuel tank 11 as compared to the cooling water temperature.

It should be understood that the invention may be modified into other forms than those specifically described herein without departing from the spirit and scope of the present invention.

Furthermore, it should be appreciated that while the various processes and routines described herein have been described as including a sequence of steps, alternative embodiments including alternative sequences of these steps and/or including alternative or supplemental steps are intended to be within the scope of the present invention.

What is claimed is:

1. A fuel nature measuring device, for measuring the nature of fuel stored in a fuel tank of an internal combustion engine, the measuring device comprising:
   a measurement passage having an orifice therein;
   gas flow generating means for generating a gas flow in said measurement passage;
   differential pressure detecting means for detecting a differential pressure between opposite ends of said orifice;
   evaporated fuel concentration operating means for determining a concentration of evaporated fuel in the fuel tank based on the differential pressure detected when said opposite ends of said measurement passage communicates with said fuel tank and the fuel in the fuel tank flows in said measurement passage;
   temperature detecting means for determining a temperature of the fuel in said fuel tank;
   volatility calculation means for calculating a volatility of the fuel in said fuel tank as the fuel nature based on the concentration of the evaporated fuel determined by said evaporated fuel concentration operation means and the temperature determined by said temperature detecting means; and
   measurement passage switching means for switching between first and second concentration measurement states,
   the first concentration measurement state being configured such that said opposite ends of said measurement passage are opened to the atmosphere and the gas passed through said measurement passage is atmospheric air,
   the second concentration measurement state being i&-configured such that said opposite ends of said measurement passage communicate with said fuel tank through a gas phase portion of said fuel tank and the fuel flows in said fuel measurement passage is the fuel from the fuel tank, wherein
   said evaporated fuel concentration operating means determines the concentration of the evaporated fuel based on a difference in detected differential pressures across said measurement passage between said first and second concentration measurement states.

2. The fuel nature measuring device according to claim 1, further comprising:
   first valve means for blocking the gas flow through said orifice, said differential pressure detecting means including a pair of lead passages having said orifice and said valve means therebetween;
   a detection space including said canister defined when said purge control valve is closed and for communicating with said measurement passage on the side of one of said leading passages;
   a communication passage to allow communicating with said measurement passage on a side of one of said leading passages;
   second valve means for blocking said communication passage; and leakage determining means for determining the presence of a leakage in said detection space based on values detected by said differential pressure detecting means in a first and a second leakage detection state, the first leakage detection state being configured such that said measurement passage is open and said communication passage is blocked, and the second leakage detection state being configured such that said measurement passage is blocked and said communication passage is open.

3. A method of measuring a nature of fuel stored in a fuel tank of an internal combustion engine, the method comprising:

generating a gas flow in a measurement passage having an orifice therein;

detecting a differential pressure between opposite ends of said orifice;

determining a concentration of evaporated fuel in the fuel tank based on the differential pressure detected when said opposite ends of said measurement passage communicates with said fuel tank and the fuel in the fuel tank flows in said measurement passage;

determining a temperature of the fuel in said fuel tank; and calculating a volatility of the fuel in said fuel tank as the fuel nature based on the determined concentration of the evaporated fuel and the determined temperature;

switching between first and second concentration measurement states, the first concentration measurement state being configured such that said opposite ends of said measurement passage are opened to the atmosphere and the gas passed through said measurement passage is atmospheric air, the second concentration measurement state being configured such that said opposite ends of said measurement passage communicate with said fuel tank through a gas phase portion of said fuel tank and the fuel flows in said fuel measurement passage is the fuel from the fuel tank, wherein determining the concentration of the evaporated fuel is determined based on a difference in detected differential pressures across said measurement passage between said first and second concentration measurement states.

4. The method according to claim 3, further comprising:

blocking the gas flow through said orifice using a first valve, said detecting the differential pressure being accomplished via a pressure detector which includes a pair of lead passages having said orifice and said first valve therebetween;

defining a detection space including said canister defined when said purge control valve is closed and for communicating with said measurement passage on the side of one of said leading passages;

providing a communication passage to allow communicating with said measurement passage on a side of one of said leading passages;

blocking said communication passage using a second valve; and determining the presence of a leakage in said detection space based on detected differential pressure values in a first and a second leakage detection state, the first leakage detection state being configured such that said measurement passage is open and said communication passage is blocked, and the second leakage detection state being configured such that said measurement passage is blocked and said communication passage is open.

* * * * *